United States Patent [19]

Maiti et al.

[11] Patent Number: 5,994,340
[45] Date of Patent: Nov. 30, 1999

[54] AZETIDINONE DERIVATIVES AS β-LACTAMASE INHIBITORS

[75] Inventors: Samarendra N. Maiti; Oludotun A. Phillips, both of Edmonton, Canada; Eduardo L. Setti, Nutley, N.J.; Andhe V. Narender Reddy, Edmonton; Ronald G. Micetich, Alberta, both of Canada; Fusahiro Higashitani, Tokushima, Japan; Chieko Kunugita, Tokushima, Japan; Koichi Nishida, Tokushima, Japan; Tatsuya Uji, Tokushima, Japan

[73] Assignee: SynPhar Laboratories, Inc., Edmonton, Canada

[21] Appl. No.: 08/920,886

[22] Filed: Aug. 29, 1997

[51] Int. Cl.$^6$ .................. A61K 31/545; A61K 31/43; C07D 205/085; C07D 409/12

[52] U.S. Cl. .................. 514/192; 514/194; 514/195; 514/196; 514/197; 514/198; 514/200; 514/201; 514/202; 514/203; 514/204; 514/205; 514/206; 514/207; 514/208; 514/209; 514/210; 540/355

[58] Field of Search .................. 514/210, 192, 514/194, 195, 196, 197, 198, 200, 201, 202, 203, 204, 205, 206, 207, 208, 209; 540/355

[56] References Cited

U.S. PATENT DOCUMENTS

| | | | |
|---|---|---|---|
| 4,816,582 | 3/1989 | Furlenmeier | 540/355 |
| 4,900,728 | 2/1990 | Heymes | 540/355 |

OTHER PUBLICATIONS

White and Handler, "The Proteins" 6th edition, p. 77, 1992.

*Primary Examiner*—Mark L. Berch
*Attorney, Agent, or Firm*—Nikaido, Marmelstein, Murray & Oram LLP

[57] ABSTRACT

New 2-oxo-1-azetidine sulfonic acid derivatives with an aminoalkyl substituted "anti" (E-isomer) oxyimino group in the acylamino substituent at the 3 position of the monobactam ring. These compounds are potent inhibitors of bacterial β-lactamases. These compounds can be used in combination with β-lactam antibiotics to increase the effectiveness of the β-lactam antibiotics in fighting infection caused by β-lactamase producing bacteria.

24 Claims, No Drawings

AZETIDINONE DERIVATIVES AS β-LACTAMASE INHIBITORS

BACKGROUND OF THE INVENTION

This invention relates to new 2-oxo-1-azetidine sulfonic acid derivatives which are of value for use in combination with β-lactam antibiotics to increase their effectiveness in infection caused by β-lactamase producing bacteria.

The most important bacterial resistance to β-lactam antibiotics is the degradation of the β-lactam nucleus by production of β-lactamase enzyme. The apparently endless capacity of β-lactamases to develop the ability to degrade the commercially used penicillins and cephalosporins, has led to the alternative strategy of seeking inhibitors to block their action. When a β-lactamase inhibitor is used in combination with a β-lactamase-susceptible β-lactam antibiotic, the effectiveness of the β-lactam antibiotic is increased or enhanced. Such an effect is known as synergy. Synergy is deemed to be exhibited by a combination of β-lactamase inhibitor and a β-lactam antibiotic when the antibacterial activity of the combination is significantly greater than the sum of the antibacterial activities of the individual components.

The present invention provides certain novel 2-oxo-1-azetidine sulfonic acid derivatives which are potent inhibitors of bacterial β-lactamases, particularly against class C β-lactamases (cephalosporinase). U.S. Pat. No. 4,775,670 issued Oct. 4, 1988 to Sykes et al. discloses the discovery of 2-oxo-1-azetidine sulfonic acid salts as antibacterial agents. One member from this series, called aztreonam is a known antibiotic. Several publications [(e.g., Antimicrobial Agents and Chemotherapy, Vol. 22, pp. 414–420, (1982); Chemotherapy, vol. 30, pp. 398–407, (1984); J. Antibiotics, vol. 35, no. 5, pp. 589–593, (1982); J. Antibiotics, vol. 43, no. 4, pp. 403–410, (1990)] suggest that aztreonam possesses β-lactamase inhibitory properties.

Aztreonam is a monocyclic β-lactam having a sulfonic acid substituent in the 1-position and a (substituted oxyimino) acylamino group in the 3-position. The orientation of the "substituted oxyimino" group in aztreonam is in the "Syn" form (Z-isomer).

The present inventors found that by introducing an aminoalkyl substituted "anti" (E-isomer) oxyimino group in the acylamino substituent at 3-position of the monobactam ring, it is possible to obtain a monobactam compound having remarkable β-lactamase inhibitory activity, particularly against class C β-lactamases (cephalosporinase).

SUMMARY OF THE INVENTION

It is an object of the present invention to provide novel and new 2-oxo-1-azetidine sulfonic acid derivatives having β-lactamase inhibitory activity, particularly against class C β-lactamases (cephalosporinases).

It is a further object of the invention to provide pharmaceutical compositions comprising a β-lactamase inhibitor of this invention in combination with a β-lactam antibiotic and a pharmaceutically acceptable carrier or diluent.

It is an additional object of the invention to provide an improved method for the treatment of bacterial infections caused by class C β-lactamase (cephalosporinase) producing bacteria in mammalian subjects, particularly in humans.

Accordingly, this invention provides novel 2-oxo-1-azetidine sulfonic acid derivatives having the formula (I)

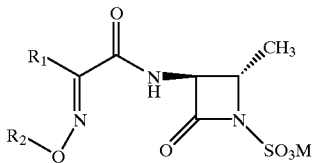

(1)

and the pharmaceutically acceptable salts thereof, wherein $R_1$ is selected from a 5-membered heterocyclic ring containing from 1 to 4 of any one or more of the heteroatoms selected from O, S and N.

$R_2$ is selected from any one of the following groups:

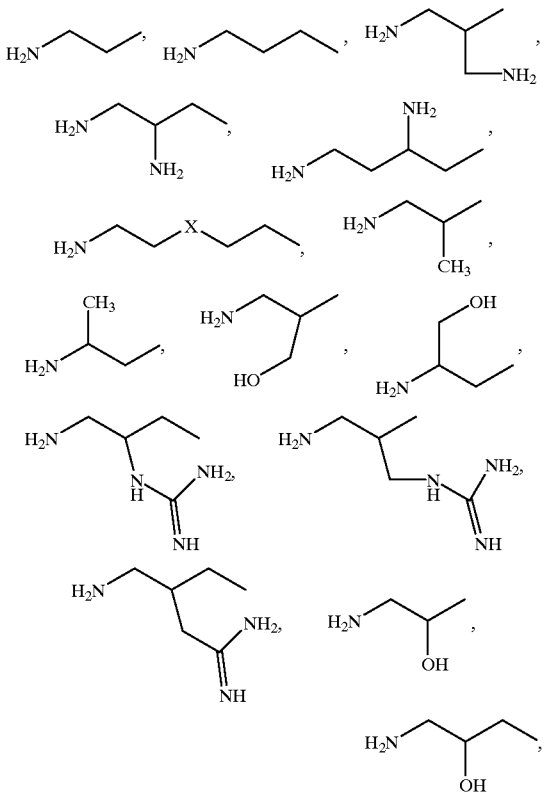

X is O, S or NH

M is hydrogen or a pharmaceutically acceptable salt forming cation.

The present inventors found that the "anti" (E-isomer) orientation of the oxyimino group (=N—$OR_2$) in the formula (I) provides excellent β-lactamase inhibitory activity and superior synergy in combination with a β-lactam antibiotic against class C β-lactamase (cephalosporinase) producing gram-negative bacteria, including *Pseudomonas aeruginosa*.

The present inventors also found that the inhibitory activity against isolated β-lactamase and the synergy with a β-lactam antibiotic is greatly influenced by the nature of the heterocyclic ring represented by $R_1$ and the nature of the substituent in the oxime fragment represented by $R_2$.

Thus, thiophene is the preferred 5-membered heterocyclic ring as $R_1$ and amino($C_{1-6}$) alkyl is the preferred group for $R_2$. Furthermore, amino($C_{1-6}$) alkyl may optionally be substituted by (C$_{1-6}$) alkyl, hydroxy (C$_{1-6}$) alkyl, amino (C$_{1-6}$) alkyl, amino, hydroxy, guanidino, amidino, guanidino (C$_{1-6}$) alkyl, amidino (C$_{1-6}$) alkyl.

DETAILED DESCRIPTION OF THE INVENTION

The β-lactamase inhibitors of this invention are the compounds having the formula (I)

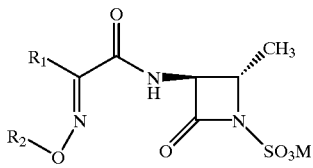

(1)

The present β-lactamase inhibitors of the invention are effective in enhancing the antimicrobial activity of β-lactam antibiotics, when used in combination to treat a mammalian subject suffering from a bacterial infection caused by a β-lactamase producing microorganism. Examples of antibiotics which can be used cojointly with the compounds of the present invention are commonly used penicillins such as amoxicillin, aspoxicillin, ampicillin, azlocillin, mezlocillin, apalcillin, hetacillin, bacampicillin, carbenicillin, sulbenicillin, ticarcillin, piperacillin, mecillinam, pivmecillinam, methicillin, ciclacillin, talampicillin, oxacillin, cloxacillin, dicloxacillin, flucloxacillin, nafcillin, pivampicillin; commonly used cephalosporins such as cephalothin, cephaloridine, cefaclor, cefadroxil, cefamandole, cefazolin, cephalexin, cephradine, cefuroxime, cefoxitin, cephacetrile, cefotiam, cefotaxime, cefsulodin, cefoperazone, ceftizoxime, cefmenoxime, cefmetazole, cephaloglycin, cefonicid, cefodizime, cefpirome, ceftazidime, ceftriaxone, cefpiramide, cefbuperazone, cefozopran, cefpimizole, cefuzonam, cefclidin, cefixime, ceftibuten, cefdinir, cefpodoxime proxetil, cefteram pivoxil, cefetamet pivoxil, cefcapene pivoxil, cefditoren pivoxil, cefepime, cefoselis, cefluprenam; commonly used carbapenems such as imipenem, meropenem, panipenem, biapenem and the like; commonly used monobactams such as aztreonam and carumonam and salts thereof. Furthermore, the β-lactamase inhibitors of the present invention can be used in combination with another β-lactamase inhibitor to enhance the antimicrobial activity of any of the above mentioned β-lactam antibiotics. For example, the inhibitors of this invention can be combined with piperacillin/tazobactam combination; ampicillin/ sulbactam combination; amoxicillin/clavulanic acid combination; ticarcillin/clavulanic acid combination, cefoperazone/sulbactam combination, and the like.

R$_1$ in the formula (I) is a 5-membered heterocyclic ring containing from 1 to 4 heteroatoms independently selected from the group consisting of O, S and N.

Preferably, R$_1$ in the formula (I) is thiophene, furan, pyrrole, 1-methyl pyrrole, 2-aminothiazole.

Even more preferably, R$_1$ is thiophene.

R$_2$ in the formula (I) is amino(C$_{1-6}$) alkyl which may optionally be substituted by any one of the following groups, such as (C$_{1-6}$) alkyl, hydroxy (C$_{1-6}$) alkyl, amino (C$_{1-6}$) alkyl, amino, amidino, hydroxy, guanidino, amidino (C$_{1-6}$) alkyl, guanidino (C$_{1-6}$) alkyl and the like. The substitution could be at the carbon atom or at the nitrogen atom of the amino group. Preferred examples of R$_2$ are the following:

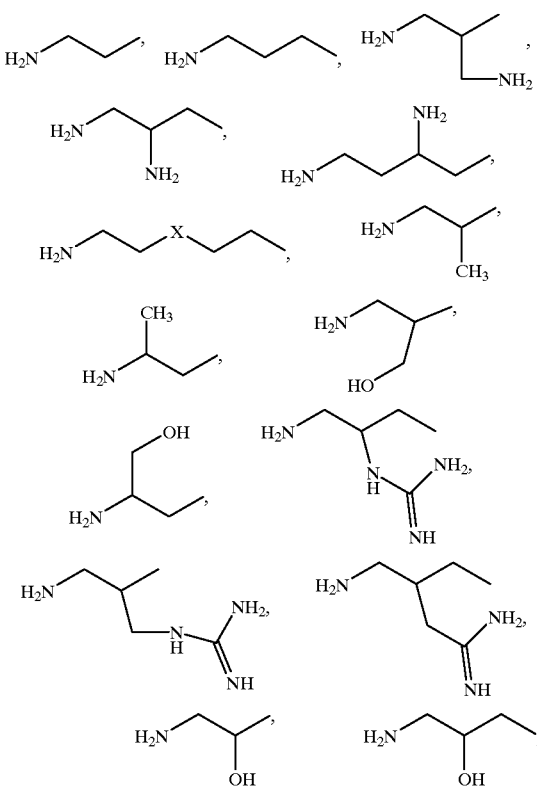

where X=O, S or NH.

Illustrative of (C$_{1-6}$)alkyl are linear or branched alkyl groups including methyl, ethyl, n-propyl, i-propyl, n-butyl, i-butyl, sec-butyl, t-butyl, pentyl and hexyl groups.

The amino groups mentioned above may remain as free amino group or it may form salts with inorganic acids or organic acids or it may form a zwitterion (inner salt) by interaction with the hydrogen atom of the sulfonic acid group [i.e., when M is hydrogen in the formula (I)].

Examples of the group for forming a pharmaceutically acceptable salt represented by M in the formula (I) include the inorganic base salts, ammonium salts, organic base salts, basic amino acid salts. Inorganic bases that can form the inorganic base salts include alkali metals (e.g., sodium, potassium) and alkaline earth metals (e.g., calcium, magnesium); organic bases that can form the organic base salts include cyclohexylamine, benzylamine, octylamine, ethanolamine, diethanolamine, diethylamine, triethylamine, procaine, morpholine, pyrrolidine, piperidine, N-ethylpiperidine, N-methylmorpholine; basic amino acids that can form the basic acid salts include lysine, arginine, ornithine, histidine and the like.

Moreover, when M is hydrogen in the formula (I) it can form a zwitterion (inner salt) by interacting with the amino group present in the molecule of formula (I) or with a basic nitrogen atom other than amino group present in the molecule.

The present invention encompasses all the possible stereoisomers as well as their racemic or optically active mixtures.

A variety of protecting groups conventionally used in the β-lactam art to protect the amino groups present in the formula (I) can be used. While it is difficult to determine which amino-protecting groups should be used, the major requirement for such a group is that it can be removed without cleaving the β-lactam ring and without reducing the double bond of the oxyimino group (=N—OR$_2$) and the protecting group must be sufficiently stable under the reaction conditions to permit easy access to the compound of formula (I). Examples of most commonly used amino-protecting groups are: trityl, tert-butoxycarbonyl, formyl, and the like.

The compounds of this invention having the formula (I) can be prepared using a variety of well known procedures as shown below:

Process A:

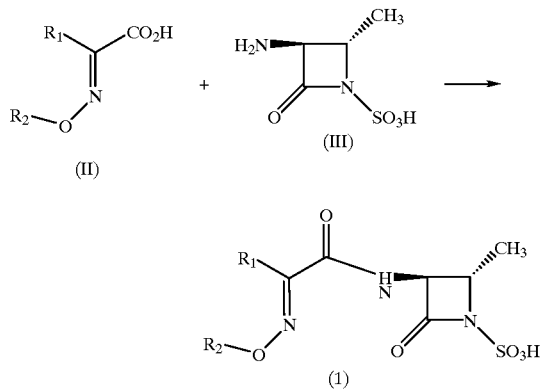

Process B:

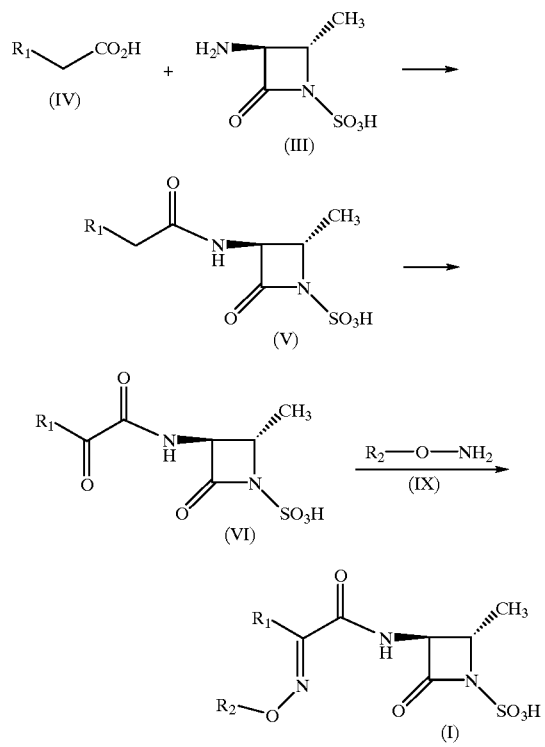

Process C:

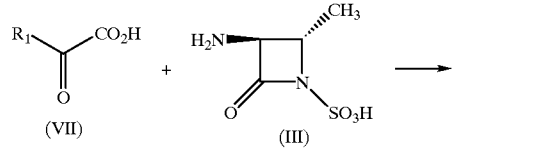

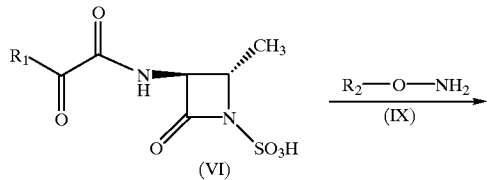

Process D:

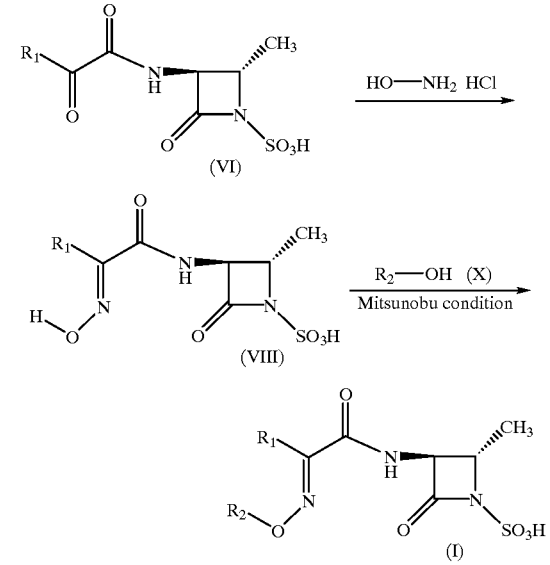

Process E:

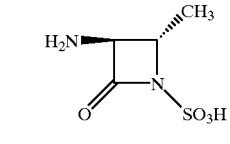

Each procedure utilizes as a starting material the known azetidine of the formula (III)

Azetidines of the formula (III) are well known in the literature; see, for example, the United Kingdom patent application no. 2,071,650 published Sep. 23, 1981; J. Org. Chem., Vol. 47, pp. 5160–5167, 1982.

In a preferred procedure, the compounds of the formula (I) can be prepared by reacting azetidines of the formula (III) with compounds of the formula

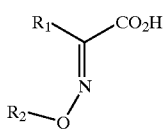

(II)

in the presence of a coupling agent. It is preferable to first treat the compound of formula (III) with one equivalent of a base, e.g. tributylamine or trioctylamine or sodium bicarbonate. Preferably the reaction is run in the presence of a substance capable of forming a reactive intermediate in situ, such as N-hydroxybenzotriazole and a catalyst such as dimethylaminopyridine, using a coupling agent such as dicyclohexylcarbodiimide. Exemplary solvents which can be used for the reaction are dimethylformamide, tetrahydrofuran, dichloromethane or mixtures thereof. Suitable reaction temperature may range from −20° C. to 50° C., preferably from 0° C. to room temperature, even more preferably at room temperature. Reaction time may range from 1 hour to 24 hours, preferably from 4 hours to 12 hours.

The reaction of an acid of formula (II) or a salt thereof, and a (3S)-3-amino-2-oxo-1-azetidinesulfonic acid salt of formula (III) proceeds most readily if the acid of formula (II) is in activated form. Activated forms of carboxylic acids are well known in the art and include acid halides, acid anhydrides (including mixed acid anhydrides), activated acid amides and activated acid esters.

To be more concrete, such reactive derivatives are:
(a) Acid anhydrides:
The acid anhydrides include, among others, mixed anhydride with a hydrohaloic acid, e.g. hydrochloric acid, hydrobromic acid; mixed anhydrides with a monoalkyl carbonic acid; mixed anhydrides with an aliphatic carboxylic acid, e.g. acetic acid, pivalic acid, valeric acid, isopentanoic acid, trichloroacetic acid; mixed anhydrides with an aromatic carboxylic acid, e.g., benzoic acid; mixed anhydride with a substituted phosphoric acid e.g., dialkoxyphosphoric acid, dibenzyloxyphosphoric acid, diphenoxyphosphoric acid, mixed anhydride with a substituted phosphinic acid e.g. diphenylphosphinic acid, dialkylphosphinic acid; mixed anhydride with sulfurous acid, thiosulfuric acid, sulfuric acid, and the symmetric acid anhydride.
(b) Activated amides:
The activated amides include amides with pyrazole, imidazole, 4-substituted imidazoles, dimethylpyrazole, triazole, benzotriazole, tetrazole, etc.
(c) Activated esters:
The activated esters include, among others, such esters as methyl, ethyl, methoxymethyl, propargyl, 4-nitrophenyl, 2,4-dinitrophenyl, trichlorophenyl, pentachlorophenyl, mesylphenyl, pyranyl, pyridyl, piperidyl and 8-quinolylthio esters. Additional examples of activated esters are esters with a N-hydroxy compound e.g., N,N-dimethylhydroxylamine, 1-hydroxy-2(1H)pyridone, N-hydroxy succinimide, N-hydroxy-phthalimide, 1-hydroxy-1H-benzotriazole, 1-hydroxy-6-chloro-1H-benzotriazole, 1,1'-bis [(6-trifluoro methyl)benzotriazolyl] oxalate (BTBO), N-ethoxycarbonyl-2-ethoxy-1,2-dihydroquinoline and the like.

Appropriate reactive derivatives of organic carboxylic acids are selected from among such ones as mentioned above depending on the type of the acid used. When a free acid is used as the acylating agent, the reaction is preferably carried out in the presence of a condensing agent. Examples of the condensing agent are N,N-dicyclohexylcarbodiimide, N-cyclohexyl-N'-morpholinoethylcarbodiimide, N'-cyclohexyl-N'-(4-diethylaminocyclohexyl) carbodiimide and N-ethyl-N'-(3-dimethylaminopropyl)carbodiimide.

The acylation reaction is usually carried out in a solvent. The solvent includes water, acetone, dioxane, acetonitrile, methylene chloride, chloroform, dichloroethane, tetrahydrofuran, ethyl acetate, dimethylformamide, pyridine and other common organic solvents inert to the reaction.

The acylation reaction can be carried out in the presence of an inorganic base such as sodium hydroxide, sodium carbonate, potassium carbonate or sodium hydrogen carbonate or an organic base such as trimethylamine, triethylamine, tributylamine, N-methylmorpholine, N-methylpiperidine, N,N-dialkylaniline, N,N-dialkylbenzylamine, pyridine, picoline, lutidine, 1,5-diazabicyclo[4.3.0] non-5-ene, 1,4-diazabicyclo [2.2.2] octane, 1,8-diazabicyclo [5.4.4] undecene-7, tetra-n-butylammonium hydroxide. The reaction is usually conducted under cooling or at room temperature.

The amides of formula V, which result from the coupling of acid IV (or a salt thereof) and a (3S)-3-amino-2-oxo-1-azetidinesulfonic acid salt of formula (III) can be oxidized to the corresponding ketoamide of formula VI (process B). A wide variety of oxidation procedures may be used e.g., potassium nitrosodisulfonate in water (or a mixed aqueous solvent), selenium dioxide in dioxane; use of metal catalysts in the presence of a suitable co-oxidant.

Alternatively, the ketoamide (VI) can be prepared (process C) by coupling the keto acid (VII) with (3S)-3-amino-2-oxo-1-azetidinesulfonic acid of formula (III) (or a salt thereof).

The compounds of this invention of formula (I) can also be prepared by reacting a ketoamide (VI) (process B or process C) having the formula

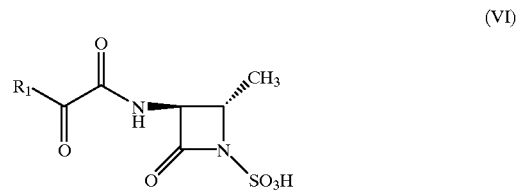

(VI)

with a hydroxylamine derivative (or a salt thereof) of formula

$R_2\text{—O—NH}_2$ (IX)

Alternatively, the ketoamide (VI) can be reacted with hydroxylamine hydrochloride to provide the hydroxyimino derivative (VIII) (process D). Coupling of the hydroxyimino derivative of formula (VIII).

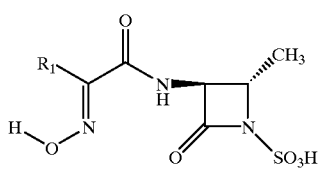

(VIII)

with the alcohol (R$_2$—OH, X) under Mitsunobu conditions (PPh$_3$/DEAD/THF) will provide the compounds of formula (I).

Alternatively, the compounds of formula (I) can be prepared by reacting the hydroxyimino derivative (VIII) (process E) with a compound of the formula (XI).

R$_2$—X  (XI)

wherein X is a leaving group such as halogen, trifluoroacetate, alkylsulfonate, arylsulfonate or other activated esters of alcohols.

The compounds of formula (I) which has a sulfo group (SO$_3$H) at N–1 position can generally react with a base to form a salt thereof. Therefore, the compound (I) may be recovered in the form of a salt and such salt may be converted into the free form or to another salt. And, the compound (I) obtained in the free form may be converted into a salt.

The present invention also covers the compound (I) in a pharmaceutically acceptable salt form. For conversion of the compound obtained in the salt form into the free form, the method using an acid can be used. Usable acids depend on the kind of protective group and other factors. Acid ion exchange resins can also be used. Solvents may be used include hydrophilic organic solvents such as acetone, tetrahydrofuran, methanol, ethanol, acetonitrile, dioxane, dimethylformamide, dimethyl sulfoxide, water and mixed solvents thereof.

Compounds of formula (II) are novel compounds and as such form an integral part of this invention. The compounds of formula (II) can be prepared by reacting an intermediate of formula (XII)

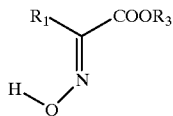

(XII)

with the alcohol R$_2$—OH (X) under standard Mitsunobu conditions (PPh$_3$/DEAD/THF; D. L. Hughes, The Mitsunobu Reaction in Organic Reactions; P. Beak et al., Eds; John Wiley & Sons, Inc: New York, Vol. 42, pp. 335–656, 1992).

R$_1$ has the same definition as defined before. R$_3$ is a protective group for the carboxyl group. The protective groups for said carboxyl group include all groups generally usable as carboxyl-protecting groups in the field of β-lactam compound and organic chemistry, for example, methyl, ethyl, propyl, isopropyl, allyl, t-butyl, benzyl, p-methoxybenzyl, p-nitrobenzyl, benzhydryl, methoxymethyl, ethoxymethyl, acetoxymethyl, pivaloyloxymethyl, trityl, 2,2,2-trichloroethyl, β-iodoethyl, t-butyldimethylsilyl, dimethylsilyl, acetylmethyl among others.

The selection of the said protective group should be in such a way which at the end of the above described reaction sequence can be cleaved from the carboxyl group under conditions that do not alter the rest of the molecule. Preferred protective groups are methyl, ethyl, allyl.

The removal of protective groups R$_3$ can be effected by selective application of a per se known method such as the method involving a base, the method involving the use of palladium tetrakis. The method involving the use of a base employs, according to the type of protective group and other conditions, inorganic bases such as the hydroxides or carbonates of alkali metals (e.g., sodium, potassium, etc.) or of alkaline earth metals (e.g., calcium, magnesium, etc.) or organic bases such as metal alkoxides, organic amines, quarternary ammonium salts or basic ion exchange resins, etc.

The reaction temperature is about 0° to 80° C. more preferably about 10° to 40° C. The reaction is usually carried out in a solvent. As the solvent, organic solvents such as ethers (e.g., dioxane, tetrahydrofuran, diethyl ether), esters (e.g., ethyl acetate, ethyl formate), halogenated hydrocarbons (e.g., chloroform, methylene chloride), hydrocarbons (e.g., benzene, toluene) and amides (e.g., dimethylformamide, dimethylacetamide) and a mixture thereof are used.

Alternatively, the intermediate of formula (II) can be prepared by reacting the compound of formula (XII) with a compound of formula R$_2$—X (XI) wherein X is a leaving group such as halogen, trifluoroacetate, alkylsulfonate, arylsulfonate or other activated esters of alcohols.

In another approach, the intermediate (II) can be prepared by reacting a keto acid compound of formula (VII) with a hydroxylamine derivative (or it's salt) of formula R$_2$—O—NH$_2$ (IX) using conventional procedures; see for example, EP 0251,299 (Kaken).

The acids useful for removing the amino-protecting group in the final step of the preparation of compound of the formula (I) are formic acid, trichloroacetic acid, trifluoroacetic acid, hydrochloric acid, hydrobromic acid, hydroiodic acid, hydrofluoric acid, trifluoromethanesulfonic acid, or the like. When the acid is used in a liquid state, it can act also as a solvent or an organic solvent can be used as a co-solvent. Useful solvents are not particularly limited as far as they do not adversely affect the reaction. Examples of useful solvents are anisole, trifluoroethanol, dichloromethane and like solvents.

The 2-oxo-1-azetidinesulfonic acid derivatives of the present invention having the formula (I) can be purified by standard procedures well-known in the art such as crystallization and chromatography over silica gel or HP-20 column.

Typical solvates of the compounds of formula (I) may include water as water of crystallization and water miscible solvents like methanol, ethanol, acetone, dioxane or acetonitrile.

Under the scope of this invention are included compounds containing variable amounts of water produced by a process such as lyophilization or crystallization from solvents containing water as a co-solvent.

Under the scope of the present invention are also included compounds containing variable amounts of acids, such as formic acid, trifluoroacetic acid, and the like which are used to remove amino-protecting groups.

Favourable pharmaceutically acceptable salts of the compounds of formula (I) are sodium, potassium and calcium.

As already mentioned, the oxyimino group, i.e., =N—OR$_2$ in the formula (I) in it's 'anti' orientation provides excellent synergy with a β-lactam antibiotic against class C β-lactamase (cephalosporinase) producing gram-negative bacteria including *P. aeruginosa*. Thus this invention includes only those compounds having the formula (I) in which the oxyimino group (=N—OR$_2$) is specifically in the 'anti' orientation (E-isomer) as shown in the formula (I).

Furthermore, the inhibitory activity against the isolated β-lactamase (cephalosporinase) and the synergy with a β-lactam antibiotic against cephalosporinase producing gram-negative bacteria are greatly influenced by the nature of the heterocyclic ring represented by R$_1$ and the nature of the substituent in the oxime fragment represented by R$_2$. Thiophene is the choice of heterocycle as R$_1$.

In the formula (I), R$_2$ is amino(C$_{1-6}$) alkyl. The amino (C$_{1-6}$) alkyl may optionally be substituted by (C$_{1-6}$) alkyl, hydroxy (C$_{1-6}$) alkyl, amino (C$_{1-6}$) alkyl, hydroxy, amino, amidino, guanidino, amidino (C$_{1-6}$) alkyl, guanidino (C$_{1-6}$) alkyl.

More preferably, R$_2$ is selected from the following groups:

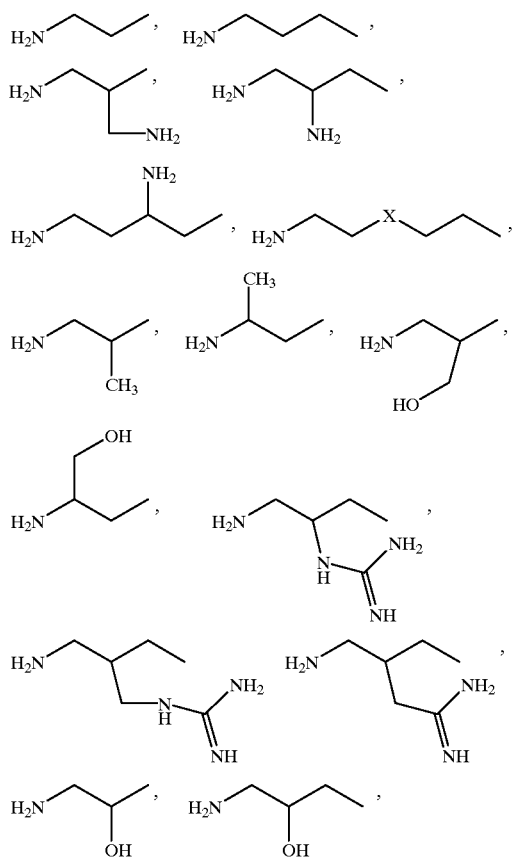

X is O, S or NH.

The compounds of the present invention including the pharmaceutically acceptable salts thereof are inhibitors of bacterial β-lactamases particularly of cephalosporinases and they increase the antibacterial effectiveness of β-lactamase susceptible β-lactam antibiotics—that is, they increase the effectiveness of the antibiotic against infections caused by β-lactamase (cephalosporinase) producing gram-negative bacteria including *Pseudomonas aeruginosa*. This makes the compounds of formula (I) and said pharmaceutically acceptable salts thereof valuable for co-administration with β-lactam antibiotics in the treatment of bacterial infections in mammalian subjects, particularly humans. In the treatment of a bacterial infection, said compound of the formula (I) or salt can be mixed with the β-lactam antibiotic, and the two agents thereby administered simultaneously. Alternatively, the said compound of formula (I) or salt can be administered as a separate agent during a course of treatment with the antibiotic.

The compounds of the invention can be administered by the usual routes, for example, parenterally e.g., by intravenous injection or infusion, intramuscularly, subcutaneously, orally, intraperitoneally; intravenous injection or infusion being the preferred. The dosage depends on the age, weight and condition of the patient and on the administration route.

The pharmaceutical compositions of the invention may contain a compound of formula (I) or a pharmaceutically acceptable salt thereof, as the active substance mixed with a β-lactam antibiotic in association with one or more pharmaceutically acceptable excipients and/or carriers.

The pharmaceutical compositions of the invention are usually prepared following conventional methods and are administered in a pharmaceutically suitable form. For instance, solutions for intravenous injection or infusion may contain as carrier, for example, sterile water or preferably, they may be in the form of sterile aqueous isotonic saline solutions.

Suspensions or solutions for intramuscular injections may contain together with the active compound of formula (I) and the β-lactam antibiotic, a pharmaceutically acceptable carrier, e.g., sterile water, olive oil, ethyl oleate, glycols, e.g., propylene glycol.

For oral mode of administration a compound of this invention of formula (I) in association with a β-lactam antibiotic can be used in the form of tablets, capsules, granules, powders, lozenges, troches, syrups, elixirs, suspensions and the like in accordance with the standard pharmaceutical practice. The oral forms may contain together with the active compound of this present invention and a β-lactam antibiotic, diluents, e.g., lactose, dextrose, saccharose, cellulose, corn starch and potato starch; lubricants e.g., silica, talc, stearic acid, magnesium or calcium stearate, and/or polyethylene glycols; binding agents e.g., starches, arabic gums, gelatin, methylcellulose, carboxymethyl cellulose, disaggregating agents, e.g., a starch, alginic acid, alginates, sodium starch glycolate, effervescing mixtures; dyestuffs; sweetners; wetting agents e.g., lecithin, polysorbates, laurylsulphates and pharmacologically inactive substances used in pharmaceutical formulations.

In most instances, an effective β-lactamase inhibiting dose of a compound of formula (I) or a pharmaceutically acceptable salt thereof, will be a daily dose in the range from about 1 to about 500 mg/kg of body weight orally, and from about 1 to about 500 mg/kg of body weight parenterally. However, in some cases it may be necessary to use dosages outside these ranges. The weight ratio of the β-lactamase inhibitor of the present invention and the β-lactam antibiotic with which it is being administered will normally be in the range of 1:20 to 20:1, preferably in the range of 1:8 to 8:1, even more preferably in the range of 1:4 to 4:1.

Test for Antibacterial Activity:

The compounds of the present invention in combination with ceftazidime and ceftazidime alone were tested for minimal inhibitory concentration (MIC) against the bacteria listed in Table 3, according to the microbroth dilution method described below. The MICs of the antibiotics (e.g., ceftazidime) alone, the MICs of ceftazidime in combination with reference compounds particularly aztreonam (Ref. compd. I) and the MICs of the β-lactamase inhibitors (10 μg/ml) of the present invention in combination with ceftazidime were determined with the same β-lactamase producing bacteria. After incubation in Mueller-Hinton Broth (Difco) at 37° C. for 18 h, the bacterial suspension was diluted and about 10⁵ CFU/ml was applied to the drug-containing Mueller-Hinton Broth in each well of 96 well plate. The MICs were recorded after 18 h of incubation at 37° C. on the lowest combinations of drug that inhibited visible growth of bacteria.

Test for β-Lactamase Inhibitory Activity:

The inhibitory activities of present compounds (β-lactamase inhibitors) against cephalosporinase from *P. aeruginosa* was measured by spectrophotometric rate assay using 490 nm and using nitrocefin as a substrate (J. Antimicrob. Chemother., vol. 28, pp 775–776, 1991). Table 1 shows the results.

The following examples are provided to demonstrate the operability of the present invention. The structures of the compounds were established by the modes of synthesis and by extensive high field nuclear magnetic resonance spectral techniques.

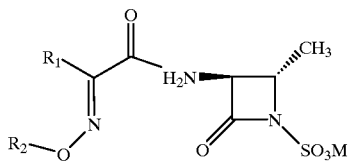

TABLE 1

β-Lactamase inhibitory activity of the prepared compounds

| Compound | $R_1$ | $R_2$/Orientation of $OR_2$ | M | $IC_{50}$, μM |
|---|---|---|---|---|
| Reference Compound I (Aztreonam) | H₂N-thiazole-CH₃ | HOOC-C(CH₃)₂-/syn | H | 0.13 |
| Reference Compound II | H₂N-thiazole-CH₃ | H₂N~~/anti | H | 0.8 |
| Compound 1 | thiophene | H₂N~~/anti | H | 0.02 |
| Compound 2 | thiophene | H₂N~~~/anti | H | 0.02 |
| Compound 3 | thiophene | H₂N-CH₂-CH(CH₃)-CH₂-NH₂ /anti | H | 0.4 |
| Compound 4 | thiophene | H₂N-CH₂-CH(NH₂)-CH₂-/anti | H | 0.065 |
| Compound 5 | thiophene | H₂N-CH₂CH₂-CH(NH₂)-CH₂-/anti | H | 0.1 |
| Compound 6 | thiophene | H₂N-CH₂CH₂-CH(NH₂)-CH₂-/anti | H | 0.1 |
| Compound 7 | thiophene | H₂N-CH₂CH₂-NH-CH₂CH₂-/anti | H | 0.08 |

TABLE 1-continued

β-Lactamase inhibitory activity of the prepared compounds

| Compound | R₁ | R₂/Orientation of OR₂ | M | IC₅₀, μM |
|---|---|---|---|---|
| Compound 8 | 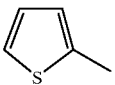 | 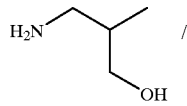 /anti | H | 0.3 |
| Compound 9 | 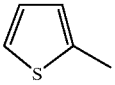 | 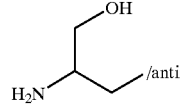 /anti | H | 0.08 |
| Compound 10 | 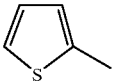 | 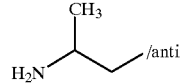 /anti | H | 0.08 |
| Compound 11 | 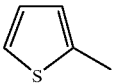 | 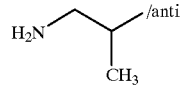 /anti | H | 0.2 |
| Compound 12 | 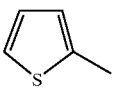 | 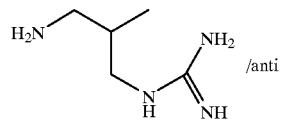 /anti | H | 1.0 |

TABLE 2

¹H NMR spectra of some representative compounds

| Compd. no. | Solvent | δ (ppm) |
|---|---|---|
| 2 | DMSO-d₆ | 9.29(d, 1H, J=8.3Hz); 7.92(dd, 1H, J=0.9 and 5.0Hz), 7.77(dd, 1H, J=0.9 and 4.0Hz); 7.71 (br, s, 3H); 7.21(dd, 1H, J=4.2 and 4.8Hz); 4.49(dd, 1H, J=2.7 and 8.2Hz); 4.39(t, 2H, J=6.0 Hz); 3.57–3.94(m, 1H); 2.85–3.04(br, t, 2H); 1.93–2.19(br, m, 2H); 1.42(d, 3H, J=6.13Hz). |
| 4 | DMSO-d₆ | 9.31(d, 1H, J=8.3Hz); 7.93(dd, 1H, J=0.9 and 5.0Hz); 7.75(dd, 1H, J=0.9 and 3.07Hz); 7.20 (dd, 1H, J=0.9 and 4.2Hz); 4.80–5.35(br, m, exchangeable with D₂O); 4.52(dd, 1H, J=2.6 and 8.2Hz); 4.13–4.40(br, s, 2H); 3.75–3.90(m, 1H); 2.60–3.40(m, 3H); 1.42(d, 3H, J=6.1Hz). |
| 5 | DMSO-d₆ | 9.25(d, 1H, J=8.2Hz); 7.91(dd, 1H, J=0.9 and 4.9Hz); 7.78(dd, 1H, J=0.9 and 3.1Hz); 7.21 (dd, 1H, J=0.9 and 4.9Hz); 5.80–6.40(br, m, 6H, exchangeable with D₂O); 4.50(dd, 1H, J=2.6 and 8.1Hz); 4.22(d, 2H); 3.75–3.90(m, 1H); 2.90–3.40(m, 3H); 1.50–1.90(m, 2H); 1.43(d, 3H, J=6.1Hz). |
| 6 | DMSO-d₆ | 9.19(d, 1H, J=8.1Hz); 7.60–8.10(m, 8H); 7.20(t, 1H, J=3.9Hz); 4.52(dd, 1H, J=2.68 and 8 20 Hz); 4.40(br, s, 1H); 3.70–3.85(m, 1H); 3.50–3.63(m, 1H); 2.70–2.90(br, s, 2H); 1.53–1.80(br, m, 4H); 1.42(d, 3H, J=6.1Hz). |
| 7 | DMSO-d₆ | 9.37(d, 1H, J=8.32Hz); 8.10–8.50(br), 7.94(dd, 1H, J=0.9 and 5. 1Hz); 7.89(dd, 1H, J=0.9 and 4Hz); 7.20(dd, 1H, J=4.02 and 5.1Hz); 4.55–4.65(br, m, 2H); 4.49(dd, 1H, J=2.4 and 8.3 Hz); 3.86(m, 1H); 3.43–3.58(br, m, 2H); 3.20–3.40(br, m, 4H); 1.42(d, 3H, J=6.1Hz). |
| 8 | DMSO-d₆ | 9.16(d, 1H, J=8.2Hz); 7.85–8.10(m, 5H); 7.20(dd, 1H, J=4.0 and 5.0Hz); 4.50–4.60(m, 2H); 3.65–3.90(m, 3H); 3.20–3.50(m, 2H); 1.45(d, 3H, J=6.1Hz). |
| 11 | DMSO-d₆ | 9.18(two sets of d, 1H, J=8.2Hz); 7.60–8.10(m, 5H); 7.20(dd, 1H, J=4.0 and 5.0Hz); 4.48–4.75 (m, 2H); 3.66–3.72(m, 1H); 3.19(d, 2H, J=5.4Hz); 1.40(t, 6H, J=6.1Hz). |
| 12 | DMSO-d₆ | 9.08(two sets of d, 1H, J=8.1Hz); 7.90–8.00(m, 6H); 7.13–7.20(m, 5H); 4.60–4.70(br, m; 1H); 4.51(dd, 1H, J=2.5 and 8.15Hz); 3.77–3.89(m, 1H); 3.50–3.65(br, m, 2H); 3.18–3.20(br, m, 2H); 1.43(d, 3H, J=6.07Hz). |

TABLE 3

Antibacterial activity of ceftazidime with compounds (β-lactamase inhibitor)

| | MIC of ceftazidime(μg/ml) | | | |
|---|---|---|---|---|
| Organism | alone | with Ref compd. I (Aztreonam) | with Ref compd. II | with compd 1 |
| E. cloacae 40054 | >32 | >32 | <0.25 | <0.25 |
| E. cloacae MNH–2 | >32 | >32 | 1.0 | 1.0 |
| E. cloacae P 99 | >32 | >32 | 32 | 1.0 |
| E. aerogenes S-95 | >32 | >32 | 1.0 | <0.25 |
| E. aerogenes 41006 | >32 | >32 | 0.5 | 0.5 |
| C. freundii CT-76 | >32 | >32 | 8.0 | 32 |
| C. freundii 44032 | >32 | >32 | 0.5 | 0.5 |
| M. morganii 36010 | >32 | >32 | 16 | 4.0 |
| M. morganii 36014 | >32 | >32 | <0.25 | <0.25 |
| M. morganii 36030 | >32 | <0.25 | 4.0 | <0.25 |
| P. aeruginosa L46004 | >32 | >32 | >32 | 8.0 |
| P. aeruginosa 46012 | >32 | >32 | >32 | 8.0 |
| P. aeruginosa 46017 | >32 | >32 | 32 | 2.0 |
| P. aeruginosa 46220 DR-2 | 16 | 16 | 8.0 | 1.0 |
| P. aeruginosa 46220 DR-2-1 | >32 | >32 | >32 | 1.0 |
| P. aeruginosa CT-122 | 16 | 16 | 8.0 | 4.0 |
| P. aeruginosa CT-137 | 8.0 | 16 | 8.0 | 2.0 |
| P. aeruginosa CT-144 | 32 | >32 | 32 | 2.0 |
| P. aeruginosa PAO 303 carb-4 | 32 | 32 | 1.6 | 2.0 |
| P. aeruginosa sp 2439 Wt. | >32 | >32 | >32 | 4.0 |
| P. aeruginosa M 1405 | >32 | >32 | >32 | 8.0 |
| P. aeruginosa M2297 | >32 | >32 | >32 | 4.0 |
| P. aeruginosa AU-1 | >32 | >32 | — | 8.0 |
| P. aeruginosa AU-5 | >32 | 1.0 | — | 4.0 |
| P. aeruginosa AU-8 | >32 | >32 | — | 16 |
| P. aeruginosa AU-10 | >32 | >32 | — | 4.0 |

| Organism | alone | with comp. 2 | with compd. 3 | with compd. 8 | with compd. 9 | with compd. 11 |
|---|---|---|---|---|---|---|
| E. cloacae 40054 | >32 | <0.25 | 0.5 | <0.25 | <0.25 | 0.5 |
| E. cloacae MNH–2 | >32 | 2.0 | 4.0 | 2.0 | 2.0 | 4.0 |
| E. cloacae P 99 | >32 | 2.0 | 2.0 | 1.0 | 1.0 | 2.0 |
| E. aerogenes S-95 | >32 | 1.0 | 1.0 | 0.5 | 0.5 | 1.0 |
| E. aerogenes 41006 | >32 | 1.0 | 2.0 | 2.0 | 1.0 | 4.0 |
| C. freundii CT-76 | >32 | >32 | 8.0 | 8.0 | >32 | >32 |
| C. freundii 44032 | >32 | 0.5 | 1.0 | 1.0 | 0.5 | 2.0 |
| M. morganii 36010 | >32 | 8.0 | 4.0 | 8.0 | 1.0 | 8.0 |
| M. morganii 36014 | >32 | <0.25 | <0.25 | <0.25 | <0.25 | <0.25 |
| M. morganii 36030 | >32 | <0.25 | <0.25 | <0.25 | <0.25 | <0.25 |
| P. aeruginosa L46004 | >32 | 32 | 16 | 32 | 32 | 16 |
| P. aeruginosa 46012 | >32 | 16 | 16 | 32 | 32 | 16 |
| P. aeruginosa 46017 | >32 | 8.0 | 8.0 | 16 | 16 | 8.0 |
| P. aeruginosa 46220DR-2 | 16 | 1.0 | 1.0 | 1.0 | 1.0 | 1.0 |
| P. aeruginosa 46220 DR-2-1 | >32 | 2.0 | 2.0 | 4.0 | 16 | 4.0 |
| P. aeruginosa CT-122 | 16 | 8.0 | 8.0 | 8.0 | 8.0 | 8.0 |
| P. aeruginosa CT-137 | 8.0 | 2.0 | 4.0 | 4.0 | 4.0 | 4.0 |
| P. aeruginosa CT-144 | 32 | 4.0 | 4.0 | 8.0 | 8.0 | 8.0 |
| P. aeruginosa PAO 303 carb-4 | 32 | 2.0 | 4.0 | 8.0 | 8.0 | 8.0 |
| P. aeruginosa sp 2439 Wt. | >32 | 16 | 8.0 | 16 | 32 | 16 |
| P. aeruginosa M 1405 | >32 | 16 | 8.0 | 32 | >32 | 16 |
| P. aeruginosa M2297 | >32 | 8.0 | 8.0 | 16 | 32 | 16 |
| P. aeruginosa AU-1 | >32 | 16 | 16 | 32 | 32 | 16 |
| P. aeruginosa AU-5 | >32 | 8.0 | 8.0 | 4.0 | 4.0 | 8.0 |
| P. aeruginosa AU-8 | >32 | 32 | 32 | — | — | — |
| P. aeruginosa AU-10 | >32 | 4.0 | 4.0 | — | — | — |

EXAMPLE 1

Preparation of compound 1

Step 1

Ethyl (E)-2-(2-thienyl)-2-(hydroxyimino) acetate

To a solution of ethyl 2-oxo-2-(2-thienyl) acetate (41 gm, 0.223 mole) in ethanol (350 ml) was added hydroxylamine hydrochloride (23.2 gm, 0.334 mole) followed by pyridine (21.6 ml, 0.267 mole) and the mixture was heated at 40–45° C. overnight. Solvent was removed under reduced pressure. Ethyl acetate (120 ml) was added and the mixture was cooled to 0° C.; the precipitated solid was collected by filtration (10 gm). The mother liquor was concentrated under reduced pressure and the residue was taken in ether (400 ml); a stream of hydrogen chloride gas was bubbled through the solution for 35 min, stirred at room temp. for 0.5 hr. After removal of the solvent, the precipitated solid was collected by filtration and washed thoroughly with ether to give an additional amount of the title compound. Ethyl (E)-2-(2-thienyl)-2-(hydroxyimino) acetate was obtained as white crystalline solid, 38 gm (92% yield).

Step 2 t-Butoxycarbonylaminoethanol

A mixture of ethanolamine (18.0 gm, 0.2947 mol) and di-tert-butyldicarbonate (64.3 gm, 0.2947 mol) in 100 ml of dioxane-water was stirred at room temp. overnight. The reaction mixture was concentrated under vacuum to about 100 ml and was then saturated with NaCl and extracted with methylene chloride. The organic extract was dried and concentrated to provide a colorless viscous oil, 47.5 gm (100% yield).

Step 3
Ethyl (E)-2-(2-thienyl-2-[1-(t-butoxycarbonylamino) ethoxyimino)] acetate To a solution of ethyl (E)-2-(2-thienyl)-2-(hydroxyimino) acetate (37.8 gm, 0.18995 mol, from step 1) and BOC-protected ethanolamine (30.62 gm, 0.18995 mol, from step 2) in dry tetrahydrofuran (400 ml) at 0° C. under nitrogen was added $PPh_3$ (49.8 gm, 0.18995 mol) portionwise and stirred for 0.5 hr. To this mixture was added diethylazodicarboxylate (35.89 ml, 0.2279 mol) dropwise and the mixture was stirred at room temperature overnight. Solvent was removed under reduced pressure and the residue was purified over a silica gel column (benzene-ethyl acetate, 9:1) to give the title compound as an oil which was solidified on cooling to give a pale yellow solid, 55 gm (86% yield).
$^1$H-NMR (DMSO-$d_6$): δ 7.90 (dd, 1H, J=0.9 and 5.0 Hz); 7.79 (dd, 1H, J=1.0 and 4.0 Hz); 7.20 (dd, 1H, J=4.0 and 5.0 Hz); 6.96 (t, 1H, J=5.5 Hz); 4.30 (m, 4H); 3.35 (m, 2H); 1.96 (s, 9H); 1.30 (t, 3H, J=7.1 Hz).

Step 4
(E)-2-(2-Thienyl)-2-[1-(t-butoxycarbonylamino) ethoxyimino)] acetic acid

A solution of ethyl (E)-2-(2-thienyl)-2-[1-(t-butoxycarbonylamino)ethoxyimino)] acetate (step 3, 16.0 gm, 46.727 mmol) in a mixture of THF—MeOH—$H_2O$ (130 ml:130 ml:65 ml) was treated with KOH (3.15 gm, 56.073 mmol) and the mixture was stirred at room temperature for 2 hr. THF and MeOH were removed under reduced pressure and the residue was diluted with water (300 ml); extracted with EtOAC (1×) and with $Et_2O$ (1×). The aqueous layer was cooled to 0° C. and pH was adjusted to 2.0 with 2(N) HCl. The mixture was extracted with methylene chloride, washed with brine, dried ($Na_2SO_4$) and concentrated to give a yellow gum (14.35 gm, 97.7% yield).
$^1$H-NMR (DMSO-$d_6$): δ 13.68 (br, s, 1H); 7.87 (dd, 1H, J=0.84 and 5.0 Hz); 7.82 (dd, 1H, J=0.84 and 3.9 Hz); 7.17 (dd, 1H, J=4.0 and 5.0 Hz); 6.95 (br, t, 1H, J=5.5 Hz); 4.27 (t, 2H, J=5.7 Hz); 3.30 (q, 2H, J=5.7 Hz); 1.34 (s, 9H).

Step 5
(3S)-trans-3-[(E)-2-(2-thienyl)-2-{1-(t-butoxycarbonylamino)ethoxyimino}acetamido]-4-methyl-2-oxoazetidine-1-sulfonic acid, potassium salt A mixture of (3S)-trans-3-amino-4-methyl-2-oxoazetidine-1-sulfonic acid, potassium salt (13.80 gm, 63.242 mmol, J. Org. Chem., 47, pp. 5160, 1982), (E)-2-(2-thienyl)-2-[1-(t-butoxycarbonylamino) ethoxyimino)] acetic acid (from step 4, 14.20 gm, 45.173 mmol), dicyclohexylcarbodiimide (9.32 gm, 45.173 mmol), and 1-HBT (6.10 gm, 45.173 mmol) in dry DMF (460 ml) was stirred at room temp. for 22 hr under $N_2$. The solid was filtered off and the filtrate was evaporated under reduced pressure to remove DMF. The gummy residue was taken in a mixture of acetonitrile-water (1:1) and the solid was filtered off. The filtrate was concentrated under reduced pressure to remove acetonitrile and freeze-dried to give an off-white solid, 34.0 gm. Purification of the product over HP-20 column using acetone-water mixture gave the title compound as a white fluffy solid, 16.4 gm (70.6% yield).
$^1$H-NMR (DMSO-$d_6$): δ 9.24 (d, 1H, J=8.36 Hz); 7.87 (dd, 1H, J=0.92 Hz); 7.83 (dd, 1H, J=0.92 Hz); 7.18 (dd, 1H, J=4.02 Hz); 6.94 (br, t, 1H, J=5.5 Hz); 4.49 (dd, 1H, J=2.68 and 8.37 Hz); 4.28 (t, 2H, J=5.8 Hz); 3.80–3.90 (m, 1H); 3.22–3.40 (m, 1H); 1.42 (d, 3H, J=6.2 Hz); 1.37 (s, 9H).

Step 6
(3S)-trans-3-[(E)-2-(2-Thienyl)-2-{(1-amino)ethoxyimino)}acetamido]-4-methyl-2-oxoazetidine-1-sulfonic acid, inner salt:

(3S)-trans-3-[(E)-2-(2-thienyl)-2-{1-(t-butoxycarbonylamino) ethoxyimino)} acetamido]-4-methyl-2-oxoazetidine-1-sulfonic acid, potassium salt (from step 5, 16.3 gm, 31.675 mmol) was dissolved in dry methylene chloride (40 ml) and cooled to −5° C. To this mixture was added trifluoroacetic acid (72.23 gm, 633.502 mmol) dropwise and stirred under nitrogen for 1 hr 20 mins. The reaction mixture was concentrated to dryness to give a gum, which was triturated with hexane (2×500 ml) and ether (2×500 ml) to give a white solid, 16.1 gm. Purification over HP-20 column using acetonitrile-water (4:1) gave the desired compound as a white solid in 59.6% yield, 7.1 gm.
$^1$H-NMR (DMSO-$d_6$): δ 9.23 (d, 1H, J=8.31 Hz); 7.88–7.95 (m, 5H); 7.22 (dd, 1H, J=4.0 and 4.9 Hz); 4.45–4.55 (m, 3H); 3.79–3.84 (m, 1H); 3.30 (t, 2H, J=5.0 Hz); 1.43 (d, 3H, J=6.1 Hz).
C, H analysis:
Calc. C, 38.29; H, 4.29; N, 14.89
Found. C, 37.62; H, 4.10; N, 14.36

EXAMPLE 2
Preparation of compound 3
Step 1
1,3-Di(t-butoxycarbonylamino)-2-hydroxy propane A solution of 1,3-diamino-2-hydroxy propane (10 gm, 0.111 mol) in a mixture of THF-water (100 ml:5 ml) was treated with di-tert-butyl dicarbonate (53.41 gm, 0.244 mol) and stirred overnight at room temperature; THF was removed under reduced pressure and the residue was taken in ether, dried over $Na_2SO_4$ and concentrated to give a gum. The residue was digested with a mixture of hexane-ether (10:1) under cooling at −70° C. The precipitated solid was collected by filtration to give the desired compound in 40% yield (12.86 gm).

Step 2
Allyl (E)-2-(2-thienyl)-2-{1,3-di(t-butoxycarbonylamino)-prop-2-oxyimino} acetate To a solution of allyl (E)-2-(2-thienyl)-2-(hydroxyimino) acetate (9.32 gm, 44.117 mmol) in dry DMF (70 ml) was added 1,3-di(t-butoxycarbonylamino)-2-hydroxy propane (from step 1, 12.86 gm, 44.2898 mmol) at 0° C. under $N_2$ followed by $PPh_3$ (11.56 gm, 44.0734 mmol) and diethylazodicarboxylate (8.29 ml, 52.96 mmol) and the mixture was stirred overnight at room temperature. The mixture was diluted with ether and washed with water. The organic layer was separated out and dried ($Na_2SO_4$) and concentrated. The crude product was purified over silica gel column using hexane-ethyl acetate mixture as eluant. The target compound was obtained as a yellow oil, 6.03 gm (28% yield).

Step 3
(E)-2-(2-Thienyl-2-{1,3-di(t-butoxycarbonylamino)-prop-2-oxyimino} acetic acid To a solution of allyl (E)-2-(2-thienyl)-2-{1,3-di(t-butoxycarbonylamino)-prop-2-oxyimino} acetate (from step 2, 6.03 gm, 12.47 mmol) in ethyl acetate (50 ml) was added sodium 2-ethyl hexanoate (2.069 gm, 12.45 mmol) followed by $PPh_3$ (326 mg, 1.245 mmol), Pd (0) $(PPh_3)_4$ (575 mg, 0.498 mmol) and the mixture was stirred at room temp. overnight. The mixture was concentrated to dryness and the residue was triturated with ether and hexane. The solid residue was taken in water (20 ml) and extracted with ether-ethyl acetate mixture (7:3). The aqueous layer was separated out and acidified with 6(N) HCl to adjust the pH~3.5 and then extracted with ethyl acetate. The ethyl acetate layer was dried and concentrated to give a foam, 4.98 gm (90% yield).

$^1$NMR (DMSO-d$_6$): δ 7.71 (d, 2H); 7.10 (t, 1H, J=4.4 Hz); 6.70–6.80 (m, 2H); 4.14–4.26 (m, 1H); 3.10–3.30 (m, 4H); 1.36 (s, 18H).

Step 4

(3S)-trans-3-[(E)-2-(2-Thienyl)-2-{1,3-di(t-butoxycarbonylamino)-prop-2-oxyimino}-acetamido]-4-methyl-2-oxoazetidine-1-sulfonic acid, potassium salt A solution of (E)-2-(2-thienyl)-2-{1,3-di(t-butoxycarbonylamino)-prop-2-oxyimino} acetic acid (step 3, Example 2, 6.12 gm, 13.799 mmol) in dry DMF (50 ml) was treated with DCC (3.409 gm, 16.52 mmol) and 1-HBT (2.232 gm, 16.52 mmol) and stirred at room temp. for 5 mins. To the mixture was added (3S)-trans-3-amino-4-methyl-2-oxoazetidine-1-sulfonic acid (2.48 gm, 13.799 mmol, *J. Org. Chem.*, 47, pp. 5160, 1982), stirred for 10 min. then KHCO$_3$ (1.38 gm, 13.79 mmol) was added. The reaction mixture was stirred overnight, DMF was removed under reduced pressure and theresidue was taken in a mixture of acetonitrile-water (7:3, 100 ml). The solid was removed by filtration and the filtrate was concentrated to a small volume and was purified over HP-20 column using water and CH$_3$CN:H$_2$O (1:4) mixture. The title compound was obtained as a solid after freeze-drying in 49% yield (4.34 gm).

$^1$H-NMR (DMSO-d$_6$): δ 9.12 (d, 1H, J=8.3 Hz); 7.85 (d, 2H); 7.16 (t, 1H, J=4.5 Hz); 6.80–6.96 (m, 2H); 4.49 (dd, 1H, J=2.6 and 8.4 Hz); 4.30–4.40 (m, 1H); 3.80–3.90 (m, 1H); 3.50–3.70 (m, 4H); 1.41 (d, 3H, J=6.2 Hz); 1.34 (s, 18H).

Step 5

(3S)-trans-3-[(E)-2-(2-Thienyl)-2-{1,3-diamino-prop-2-oxyimino} acetamido]-4-methyl-2-oxoazetidine-1-sulfonic acid, triflate salt To a solution of (3S)-trans-3-[(E)-2-(2-thienyl)-2-{1,3-di(t-butoxycarbonylamino)-prop-2-oxyimino} acetamido]-4-methyl-2-oxoazetidine-1-sulfonic acid, potassium salt (step 4, Example 2, 4.04 gm, 5.2756 mmol) in methylene chloride (12 ml) cooled to −5° C. was added trifluoroacetic acid (18 gm, 156.890 mmol) dropwise and stirred at this temperature for 4 hr. The mixture was diluted with methylene chloride and concentrated under reduced pressure to give a foam which was triturated with ether to afford a white solid. Purification of the product over HP-20 column with acetonitrile-water (1:9) as eluant and freeze-drying of the desired fractions gave the target compound as a white solid, 2.15 gm (66% yield). $^1$H-NMR (DMSO-d$_6$): δ 9.04 (d, 1H, J=8.05 Hz); 7.96–8.05 (m, 8H); 7.24 (t, 1H, J=4.5 Hz); 4.70–4.90 (m, 1H); 4.53 (dd, 1H, J=2.68 and 8.04 Hz); 3.70–3.84 (m, 1H); 3.18–3.40 (m, 4H); 1.44 (d, 3H, J=6.07 Hz).

C, H analysis:

Calc. C, 34.68; H, 3.88; N, 13.48

Found. C, 34.37; H, 3.74, N, 12.97

EXAMPLE 3

Preparation of compound 10

Step 1

2-t-Butoxycarbonylamino-1-propanol

A solution of 2-amino-1-propanol (10.2 gm, 136 mmol) in 1,4-dioxane (250 ml) was cooled to 0° C. and was treated with di-tert-butyldicarbonate (29.64 gm, 136 mmol). After stirring at 0° C. for 30 min, the mixture was allowed to stir at room temp for 20 hrs. Evaporation of the reaction mixture gave a colorless oil which on treatment with hexane at 0° C. gave white crystals.

$^1$H-NMR (DMSO-d$_6$): δ 6.50 (d, 1H, J=7.5 Hz); 4.57 (t, 1H, J=5.7 Hz); 3.07–3.49 (m, 3H); 1.44 (d, 3H, J=6.5 Hz); 1.36 (s, 9H).

Step 2

Allyl (E)-2-(2-thienyl)-2-{2-(t-butoxycarbonylamino)-prop-1-oxyimino} acetate

A mixture of allyl (E)-2-(2-thienyl)-2-(hydroxyimino) acetate (4.91 gm, 23.25 mmol) and 2-t-butoxycarbonylamino-1-propanol (step 1, Example 3, 3.794 gm, 23.225 mmol) in dry THF (150 ml) was cooled to 0° C. under nitrogen. To this mixture was added PPh$_3$ (6.71 gm, 25.58 mmol) followed by dropwise addition of diethyl azodicarboxylate (4.03 ml, 25.558 mmol). The mixture was stirred at 0° C. for 30 min and at room temperature for 24 hr. Solvent was removed under reduced pressure and the residue was purified over a silica gel column chromatography using hexane-ethyl acetate mixture (8:2) to give the title compound as an oil in 83.8% yield (7.17 gm).

$^1$H NMR (DMSO-d$_6$): δ 7.92 (dd, 1H, J=1.0 and 4.2 Hz); 7.76 (dd, 1H, J=1.0 and 4.0 Hz); 7.20 (t, 1H, J=4.0 Hz); 6.86 (d, 1H, J=8.4 Hz); 5.92–6.10 (m, 1H); 5.27–5.45 (m, 2H); 4.82 (d, 2H, J=5.5 Hz); 4.21 (d, 1H, J=4.1 Hz); 4.18 (d, 1H, J=2.8 Hz); 3.80–3.95 (m, 1H); 1.33 (s, 9H); 1.08 (d, 3H, J=6.8 Hz).

Step 3

(E)-2-(2-Thienyl)-2-{2-(t-butoxycarbonylamino)-prop-1-oxyimino} acetic acid

A mixture of allyl (E)-2-(2-thienyl)-2-[2-(t-butoxycarbonylamino)-prop-1-oxyimino] acetate (from step 2, Example 3, 5.446 gm, 14.82 mmol), PPh$_3$ (0.389 gm, 1.48 mmol) and sodium ethyl hexanoate (2.463 gm, 14.82 mmol) in ethyl acetate (80 ml) was treated with Pd (0) (PPh$_3$)$_4$ (0.685 gm, 0.59 mmol) at room temperature. The mixture was stirred at room temp. for 4 hr. the mixture was treated with water and the aqueous layer was separated out, cooled to 0° C. and the pH was adjusted to 2.0 with 1(N) HCl. The acidified aqueous layer was extracted with methylene chloride, dried and concentrated to give the desired title compound as a gummy foam (4.74 gm, 97.5%).

$^1$H NMR (DMSO-d$_6$): δ 7.87 (dd, 1H, J=1.0 and 4.0 Hz); 7.79 (dd, 1H, J=1.0 and 4.0 Hz); 7.17 (dd, 1H, J=1.0 and 4.0 Hz); 6.85 (d, 1H, J=8.4 Hz); 4.13 (t, 2H); 3.82–8.96 (m, 1H); 1.33 (s, 9H); 1.08 (d, 1H, J=6.7 Hz).

Step 4

(3S)-trans-3-[(E)-2-(2-Thienyl)-2-{2-(t-butoxycarbonylamino)-prop-1-oxyimino} acetamido]-4-methyl-2-oxoazetidine-1-sulfonic acid, potassium salt A mixture of (E)-2-(2-thienyl)-2-[2-(t-butoxycarbonylamino)-prop-1-oxyimino]acetic acid (from step 3, Example 3, 3.43 gm, 10.445 mmol), DCC (2.263 gm, 10.97 mmol), 1-HBT (1.482 gm, 10.97 mmol) and (3S)-trans-3-amino-4-methyl-2-oxoazetidine-1-sulfonic acid (J. Org. Chem., 47, pp. 5160, 1982, 1.882 gm, 10.445 mmol) in dry DMF (40 ml) was stirred under nitrogen at room temp. for 10 min. Solid KHCO$_3$ (1.05 gm, 10.445 mmol) was added in one portion and the mixture was stirred at room temp. for 24 h. Solid was removed by filtration and the filtrate was concentrated under reduced pressure to remove DMF. The gummy residue was treated with a mixture of acetonitrile-water (1:1) and the preceipitated solid was filtered off. The filtrate was concentrated to give a gummy residue which was purified over HP-20 column using a gradient mixture of acetonitrile-water to give the pure title compound in 56% yield (3.1 gm). $^1$H NMR (DMSO-d$_6$): δ 9.23 (d, 1H, J=8.4 Hz); 7.86 (dd, 1H, J=1.0 and 4.0 Hz), 7.78 (dd, 1H, J=1.0 and 4.0 Hz); 7.16 (t, 1H); 6.89 (d, 1H, J=8.0 Hz); 4.47 (dd, 1H, J=1.0 and 7.0 Hz); 4.15 (t, 2H); 3.80–4.00 (m, 2H); 1.39 (d, 3H, J=6.2 Hz); 1.33 (s, 9H); 1.09 (d, 1H, J=6.7 Hz).

Step 5
(3S)-trans-3-[(E)-2-(2-Thienyl-2-{(2-amino)-prop-1-oxyimino} acetamido]-4-methyl-2-oxoazetidine-1-sulfonic acid, inner salt (compound 10)

A solution of (3S)-trans-3-[(E)-2-(2-thienyl)-2-{2-(t-butoxycarbonylamino)-prop-1-oxyimino} acetamido]-4-methyl-2-oxoazetidine-1-sulfonic acid, potassium salt (from step 4, Example 3, 3.05 gm, 5.77 mmol) in dry methylene chloride was cooled to 0° C. under nitrogen; trifluoroacetic acid (19.74 gm, 13.3 ml, 173 mmol) was added and the mixture was stirred at 0° C. for 2 h. Volatile solvents were removed and the residue was triturated with ether. The solid thus obtained was purified over HP-20 column to give the pure product after freeze drying (1.7 gm, 75.46% yield).
$^1$H-NMR (DMSO-d$_6$): δ 9.23 (d, 1H, J=8.1 Hz); 7.80–8.00 (m, 5H); 7.21 (t, 1H); 4.50 (dd, 1H, J=2.6 and 5.6 Hz); 4.35 (d, 2H, J=5.5 Hz); 3.77 (dd, 1H, J=2.5 and 3.6 Hz); 3.71 (q, 1H, J=5.7 Hz); 1.42 (d, 1H, J=6.2 Hz); 1.25 (d, 1H, J=6.6 Hz).

EXAMPLE 4

Preparation of compound 9
Step 4
(3S)-trans-3-[(E)-2-(2-Thienyl)-2-{1-hydroxy-2-(t-butoxycarbonylamino)-prop-3-oxyimino}acetamido]-4-methyl-2-oxoazetidine-1-sulfonic acid, postassium salt A mixture of (E)-2-(2-thienyl)-2-{1-hydroxy-2-(t-butoxycarbonylamino)-prop-3-oxyimino} acetic acid (11.0 gm, 0.033 mol), DCC (6.8 gm, 0.033 mol), 1-HBT (4.46 gm, 0.033 mol) and (3S)-trans-3-amino-4-methyl-2-oxoazetidine-1-sulfonic acid (J. Org. Chem., 47, pp. 5160, 1982, 6.2 gm, 0.033 mol) in dry DMF (20 ml) was stirred under nitrogen at room temperature for 10 min. Solid KHCO$_3$ (3.3 gm, 0.033 mol) was added in one portion and the mixture was stirred at room temperature overnight. Solvent was removed under reduced pressure and the residue was purified over a HP-20 column using water-acetonitrile (9:1) as eluant. The title compound was obtained as a white fluffy solid in 39% yield (6.9 gm).
$^1$H NMR (DMSO-d$_6$): δ 9.23 (d, 1H, J=8.3 Hz); 7.85 (dd, 1H, J=1.0 and 5.0 Hz); 7.81 (d, 1H, J=3.8 Hz); 7.17 (t, 1H, J=5.0 Hz); 6.74 (d, 1H, J=8.5 Hz); 4.48 (dd, 1H, J=2.6 and 8.2 Hz); 4.30 (m, 3H); 3.86 (dd, 1H, J=2.6 and 6.1 Hz); 3.86 (m, 1H); 3.45 (m, 2H); 1.42 (d, 3H, J=6.1 Hz); 1.34 (s, 9H).
Step 5
(3S)-trans-3-[(E)-2-(2-Thienyl)-2-{1-hydroxy-2-amino-prop-3-oxyimino} acetamido]-4-methyl-2-oxoazetidine-1-sulfonic acid, inner salt (compound 9)

(3S)-trans-3-[(E)-2-(2-thienyl)-2-{1-hydroxy-2-(t-butoxycarbonylamino)-prop-3-oxyimino} acetamido]-4-methyl-2-oxoazetidine-1-sulfonic acid, potassium salt (from step 4, Example 4; 5.13 gm, 9.7 mol) was dissolved in a mixture of TFA/anisole (1:1) at room temperature and the mixture was stirred at room temp. for 3 hr under nitrogen. Volatile solvents were removed under reduced pressure and the residue was dissolved in water and freeze-dried. The crude product was purified over a HP-20 column using water-acetonitrile (9:1) as eluant. The title compound was obtained as a white fluffy mass after freeze-drying, 2.01 gm (46% yield).
$^1$H-NMR (DMSO-d$_6$): δ 9.25 (d, 0.5H, J=8.1 Hz); 9.23 (d, 0.5H, J=8.1 Hz); 8.03 (br, s, 3H); 7.94 (d, 1H, J=5.0 Hz); 7.84 (d, 1H, J=3.0 Hz); 7.21 (dd, 1H, J=3.0 and 5.0 Hz); 5.42 (br, s, 1H; 4.50 (m, 1H); 4.43 (m, 2H); 3.63 (m, 4H); 3.30 (br, s, 1H); 1.42 (d, 3H, J=6.1 Hz).

What we claim:
1. A compound of formula (I)

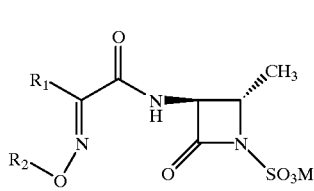

(1)

wherein R$_1$ is a 5-membered heterocyclic ring containing from 1 to 4 heteroatoms independently selected from O, S and N;

R$_2$ is an amino (C$_{1-6}$) alkyl which is unsubstituted or substituted by one or more of the following groups: (C$_{1-6}$) alkyl, hydroxy (C$_{1-6}$) alkyl, amino (C$_{1-6}$) alkyl, hydroxy, amino, amidino, guanidino, amidino (C$_{1-6}$) alkyl, and guanidino (C$_{1-6}$) alkyl; or R$_2$ is selected from the group consisting of

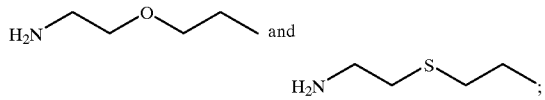

M is hydrogen or a pharmaceutically acceptable salt forming non-toxic cation, wherein the oxyimino group (=N—OR$_2$) in formula (I) is specifically in the 'anti' orientation (E-isomer); and hydrates or pharmaceutically acceptable salts thereof.
2. The compound according to claim 1, where the R$_1$ group in the formula (I) is 2-thienyl.
3. The compound according to claim 1 where R$_2$ is selected from any one of the following groups:

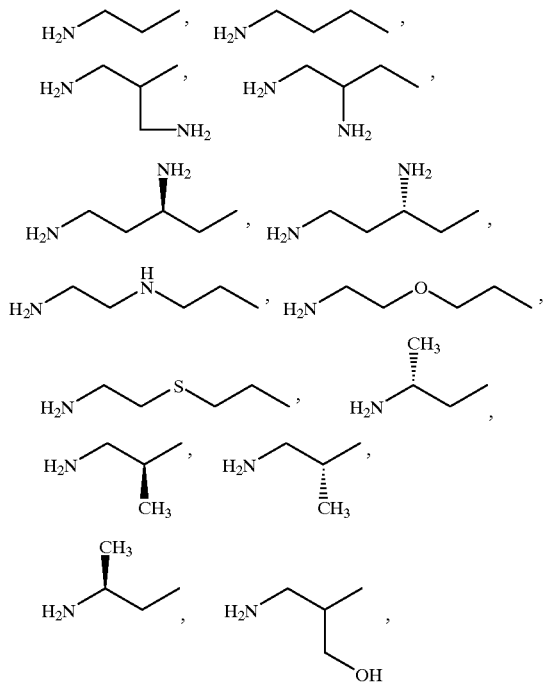

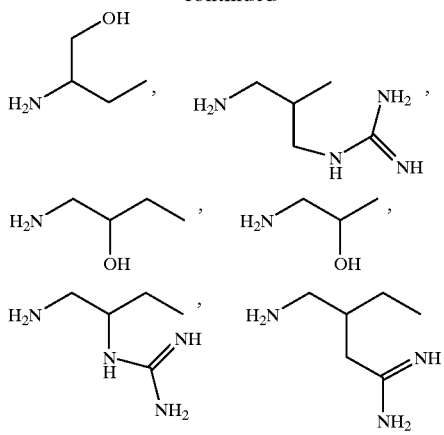

4. A hydrate of the compound according to claim 1 wherein said hydrate contains variable amounts of water.

5. The hydrate according to claim 4, wherein said variable amounts of water result from lyophilization, crystallization or column purification.

6. A compound according to claim 1, when M is hydrogen.

7. A pharmaceutically acceptable salt of the compound according to claim 1 wherein said pharmaceutically acceptable salt is an acid addition salt formed by reaction with inorganic acids or organic acids.

8. A pharmaceutical composition suitable for the treatment of bacterial infections in mammals comprising the compound described in claim 1 or a pharmaceutically acceptable salt thereof and a pharmaceutically acceptable carrier.

9. A pharmaceutical composition suitable for the treatment of bacterial infections comprising the compound according to claim 1 or a pharmaceutically acceptable salt thereof, a β-lactam antibiotic and a pharmaceutically acceptable carrier.

10. The method for treating bacterial infections comprising administering an effective amount of β-lactam antibiotic and a compound according to claim 1 or a pharmaceutically acceptable salt thereof to a subject in need of such treatment.

11. The method for treating bacterial infections comprising administering an effective amount of β-lactam antibiotic and a compound according to claim 6 to a subject in need of such treatment.

12. An antibiotic composition comprising the compound described in claim 6 and a β-lactam antibiotic composition.

13. The pharmaceutical composition according to claim 9 wherein said β-lactam antibiotic is selected from the group consisting of penicillins, cephalosporins, carbapenems and monobactams.

14. The pharmaceutical composition according to claim 13, wherein said penicillins are selected from the groups consisting of amoxicillin, ampicillin, azlocillin, mezlocillin, apalcillin, hetacillin, bacampicillin, carbenicillin, sulbenicillin, ticarcillin, piperacillin, mecillinam, pivmecillinam, methicillin, ciclacillin, talampicillin, aspoxicillin, oxacillin, cloxacillin, dicloxacillin, flucoxacillin, nafcillin, pivampicillin, piperacillin in combination with tazobactam, ampicillin in combination with sulbactam, amoxicillin in combination with clavulanic acid, ticarcillin in combination with clavulanic acid.

15. The pharmaceutical composition according to claim 13, wherein said cephalosporins are selected from the groups consisting of cephalothin, cephaloridine, cefaclor, cefadroxil, cefamandole, cefazolin, cephalexin, cephradin, cefuroxime, cefoxitin, cephacetrile, cefotiam, cefotaxime, cefsulodin, cefoperazone, ceftizoxime, cefmenoxime, cefmetazole, cephaloglycin, cefonicid, cefodizime, cefpirome, ceftazidime, ceftriaxone, cefpiramide, cefbuperazone, cefuzonam, cefpimizole, cefozopran, cefepime, cefoselis, cefluprenam, cefclidin, cefixime, ceftibuten, cefdinir, cefpodoxime proxetil, cefteram pivoxil, cefetamet pivoxil, cefcapene pivoxil, cefditoren pivoxil, cefoperazone in combination with sulbactam.

16. The pharmaceutical composition according to claim 13, wherein said carbapenems are selected from the group consisting of imipenem, meropenem, biapenem and panipenem and said monobactams are selected from the group consisting of aztreonam and carumonam.

17. The pharmaceutical composition according to claim 13, wherein said compound and a β-lactam antibiotic are contained in the range of 1:20 to 20:1 weight ratios.

18. The method for inhibiting a β-lactamase inactivation of an antibiotic containing a β-lactam antibiotic, which comprises administering to a patient an effective amount of the compound described in claim 1 or a pharmaceutically acceptable salt thereof.

19. The method for inhibiting a β-lactamase inactivation of an antibiotic containing a β-lactam antibiotic, which comprises administering to a patient an effective amount of the compound described in claim 6.

20. A pharmaceutical composition comprising the compound of claim 2, a β-lactam antibiotic, and a pharmaceutically acceptable excipient.

21. The method according to claim 11, wherein the β-lactam antibiotic and said compound are administered separately.

22. The method according to claim 10, wherein the β-lactam antibiotic and said compound are administered simultaneously.

23. The method according to claim 11, wherein the β-lactam antibiotic and said compound are administered simultaneously.

24. The method according to claim 10, wherein the β-lactam antibiotic and said compound are administered separately.

* * * * *